United States Patent [19]

Tarancon

[11] Patent Number: 5,229,072
[45] Date of Patent: Jul. 20, 1993

[54] USE OF INTERHALOGEN COMPOUNDS AS A STERILIZING AGENT

[75] Inventor: Gregorio Tarancon, Woodbridge, N.J.

[73] Assignee: Liquid Carbonic Inc., Scarborough, Canada

[21] Appl. No.: 829,417

[22] Filed: Feb. 3, 1992

[51] Int. Cl.$^5$ ............................................. A01N 59/10
[52] U.S. Cl. ................... 422/37; 252/182.32; 252/183.14
[58] Field of Search ............ 422/37; 252/182.32, 252/183.14; 424/623

[56] References Cited

U.S. PATENT DOCUMENTS

| | | | |
|---|---|---|---|
| 2,913,366 | 11/1959 | Goebel | 167/17 |
| 3,269,899 | 8/1966 | Parker | 167/39 |
| 3,854,886 | 12/1974 | Pursley | 23/260 |
| 3,956,470 | 5/1976 | Gould et al. | 423/466 |
| 4,822,513 | 4/1989 | Corby | 422/37 |
| 4,954,316 | 9/1990 | Globus | 422/37 |

FOREIGN PATENT DOCUMENTS 836016 6/1960 United Kingdom .

Primary Examiner—Robert J. Warden
Assistant Examiner—Timothy M. McMahon
Attorney, Agent, or Firm—Fitch, Even, Tabin & Flannery

[57] ABSTRACT

A method for sterilizing the surface of an article contaminated with bacteria and bacterial spores which comprises exposing the surface to an effective amount of a fluorine interhalogen compound sterilizing agent such as gaseous chlorine trifluoride or chloride pentafluoride, or mixtures thereof. The surface to be sterilized can be subjected to a gaseous atmosphere of controlled humidity immediately prior to or during exposure to the gaseous sterilant.

33 Claims, No Drawings

USE OF INTERHALOGEN COMPOUNDS AS A STERILIZING AGENT

BACKGROUND OF THE INVENTION

This invention relates to the sterilizing of articles contaminated with bacteria and bacterial spores and, more particularly, relates to the use of a fluorine interhalogen compound, such as chlorine trifluoride or chlorine pentafluoride as a chemosterilizing agent for sterilizing surfaces contaminated with bacteria and bacterial spores.

The use of gaseous chemical agents as an antimicrobial agent is known. Microbiocides for destroying bacterial and fungal spores and viruses are typified by gaseous ethylene oxide and formaldehyde. However, ethylene oxide is difficult to handle at concentrations and temperatures required for effective sterilization, such as at concentrations of 10% by volume, in that ethylene oxide at concentrations in excess of 3% by volume in air is violently explosive. In addition, ethylene oxide is flammable and toxic at lower concentrations. Ethylene oxide penetrates well into porous materials and, in that it is strongly absorbed by rubber and plastics, the vapours are not easily eliminated by aeration.

The use of gaseous formaldehyde may be undesirable in that it is likely to leave a residue of solid paraformaldehyde if applied in the high concentrations effective for sterilization. Also, formaldehyde gas does not penetrate effectively into porous and permeable materials.

Chlorine dioxide is also known as an effective chemosterilizing agent. U.S. Pat. No. 4,681,739 issued Jul. 21, 1987 to Rosenblatt et al discloses the use of chlorine dioxide gas with an inert carrier gas such as nitrogen for killing bacterial spores. The surface of an gaseous atmosphere effective to enhance the susceptibility of the spores to subsequent chemosterilization with the chlorine dioxide gas and an inert carrier gas.

It is an object of the present invention to provide an effective and stable chemosterilizing agent at low levels of concentration.

SUMMARY OF THE INVENTION

The present invention relates to the use of fluorine interhalogen compounds as an effective chemosterilizing agents. In its broad aspect, the present invention comprises a method for sterilizing the surface of an article contaminated with bacteria and bacterial spores comprising the steps of exposing the surface to an effective amount of a fluorine interhalogen compound to kill the bacteria and bacterial spores.

DETAILED DESCRIPTION OF THE INVENTION

More particularly, the present invention comprises exposing the surface of an article contaminated with bacteria and bacterial spores with an atmosphere containing a gaseous fluorine interhalogen compound or suspended droplets of a liquid fluorine interhalogen compound or a combination thereof, in an amount of 50 to 10,000 parts per million (ppm) by volume, preferably about 100 to 1000 ppm by volume, for a time period sufficient to kill the bacteria and bacterial spores Most preferably, the atmosphere contains a fluorine interhalogen compound at about 750 ppm and the surface is contacted with the atmosphere at room temperature for a time period of at least about 15 minutes to 4 hours. The balance of the atmosphere is preferably an inert carrier gas, such as nitrogen, carbon dioxide or air.

The fluorine interhalogen compound is preferably selected from those compounds which are gaseous at ambient room temperature. The gaseous fluorine interhalogen compounds include chlorine trifluoride, chlorine pentafluoride and iodine heptafluoride. Fluorine interhalogen compounds which are liquid at ambient room temperature may also be used if they are suspended as droplets in a carrier gas. At the levels of use of the present invention (50–10,000 ppm), the liquid fluorine interhalogen compounds are readily entrained in the carrier gas in the same manner as water vapor is entrained in air to provide humidity. The liquid fluorine interhalogen compounds include bromine heptafluoride, bromine pentafluoride and iodine pentafluoride.

The relative humidity (RH) of an indoor environment rarely rises above about 60% and is often below about 25% RH. Bacterial spores present on an essentially moisture-free substrate and exposed to low indoor ambient humidities will be in a low moisture or desiccated state. It is well recognized in the art that desiccated spores possess a high degree of resistance to chemical sterilizing agents. Thus, surfaces contaminated with desiccated spores will require more rigorous sterilizing conditions than would be required to sterilize the same type of spore in a non desiccated state.

In accordance with another embodiment of the present invention, the susceptibility of desiccated spores to chemosterilization with a fluorine interhalogen compound is enhanced by exposing the spores to a gaseous atmosphere of controlled humidity immediately prior to and/or during exposure of the spores to the fluorine interhalogen compound. This allows the use of lower concentrations of the fluorine interhalogen compound and/or shorter exposure times if the above humidification procedure were not followed.

In accordance with the preferred embodiment of the humidification procedure of this invention, desiccated spores are briefly humidified by exposure to highly humid air having a relative humidity of above 65%; more preferably in the range of about 65% to about 95% RH, for at least 15 minutes immediately prior to the step of adding the fluorine interhalogen compound to the spores. Humidification may be conducted at about ambient room temperature, although lower or higher temperatures may be used.

Although the description of the invention will now proceed with reference to the use of chlorine that an equivalent amount of other fluorine interhalogen compounds may be employed.

The concentration of the chlorine trifluoride gas employed in conjunction with the foregoing humidification procedure preferably ranges from about 0.2 to 4.0 milligrams per liter (mg/L) (50 to 1000 ppm). The article undergoing sterilization is exposed to the gaseous sterilant for about 15 minutes to about 4 hours. The dwell time can vary inversely with the sterilant concentration, so that the concentration of chlorine trifluoride can be lowered if longer dwell times are acceptable.

The humidification procedure may be carried out using conventional apparatus. For example, the article contaminated with spores may be placed in a closed chamber and a vacuum drawn on the chamber. Water is then introduced by passing humidified air through the chamber for at least 15 minutes, then the chlorine trifluoride sterilant gas is introduced into the humidified chamber. The bacterially contaminated article is exposed to the gaseous environment for a period sufficient to sterilize the materials being treated, e.g. for about 15 minutes to about 4 hours, and preferably about 30 minutes to 2 hours.

In further embodiments of the humidification procedure of this invention, a stream of moist air and a separate stream of chlorine trifluoride in an inert carrier gas such as nitrogen, carbon dioxide or air, may be introduced at the same time or as a mixture into an exposure chamber containing the spore-contaminated object. The sterilization may be conducted at room temperature to about 35° C. or at higher temperature such as at 100° C. or above in a steam atmosphere. The RH of the chlorine trifluoride atmosphere preferably is maintained above about 65%, and most preferably about 65% to 95%, for low temperature applications.

The sterilization process of the present invention may so be employed to sterilize articles contained in packaging which is permeable to the fluorine interhalogen compounds and preferably packaging which is also permeable to moisture. For example, this process may be employed to sterilize medical or dental implements which have been packaged in gas permeable packaging under non-sterile conditions.

The present invention provides a method for sterilizing microbiologically contaminated articles, such as dry and gas impermeable surfaces of medical or dental implements or other articles contaminated with live bacteria and bacterial spores.

Chlorine trifluoride, for example, can be packaged in high pressure cylinders at a pressure of about 2000 pounds per square inch (psi) at a concentration of about 1% by volume in nitrogen. A cylinder of 1% by volume mixture of chlorine trifluoride and nitrogen can be diluted in a blender to a concentration of a out 1000 ppm.

The sterilizing procedure may be carried out using conventional apparatus such as, for example, a closed chamber into which the contaminated article has been placed. The chamber is evacuated to create a partial trifluoride gas is injected into the chamber. After the spore contaminated article has been exposed to the chlorine trifluoride for about 15 minutes to about 4 hours, preferably about 30 minutes to 2 hours, the chlorine trifluoride is drawn into a solid scrubber for removal and disposal.

The method of the invention will now be described with reference to the following non-limitative examples.

The spores of the standard test organism employed to determine the effective sterilizing concentration of chlorine trifluoride were those of Bacillus subtilis. To rate the effectiveness of a given concentration of chlorine trifluoride, an initial population of $10^5$–$10^7$ spores sterilized by the method of the invention, as described below, showed no growth on the nutrient medium after 3 days of observation following exposure to said concentration.

Tests were carried out using a stainless steel manifold and eight 500 milliliter closed sterilizing chambers. The spores were placed on stainless steel plaques in each of the chambers with approximately $10^6$ spores per plaque. The sterilizing chambers were humidified by passing moist air (R. H. greater than 70%) through the chambers for 15 minutes. The dwell time was increased for each pair of chambers, the temperature of the chambers was maintained at about 25° C., and the concentration of the chlorine trifluoride was maintained at about 870 ppm. The data for this illustrative test is outlined in Table I below and it will be noted that dwell times of 15 minutes and greater permitted complete sterilization of bacterial spores.

TABLE I

| Chamber Number | Dwell time(min.) | Spore Count (bacteria/ml) |
| --- | --- | --- |
| Control | 0 | $8.5 \times 10^5$ |
| 1 & 2 | 15 | none |
| 3 & 4 | 30 | none |
| 5 & 6 | 45 | none |
| 7 & 8 | 60 | none |

It will be understood, of course, that modifications can be made in the embodiment of the invention illustrated and described herein without defined by the appended claims.

I claim:

1. A method for sterilizing the surface of an article contaminated with bacterial spores comprising the step of said surface to an effective amount of a gaseous atmosphere containing at least one gaseous fluorine interhalogen compound for a time sufficient to kill said spores.

2. A method as claimed in claim 1 in which said fluorine interhalogen compound is selected from the group consisting of chlorine trifluoride, chlorine pentafluoride, iodine heptafluoride, bromine trifluoride and bromine pentafluoride.

3. A method as claimed in claim 2 in which the surface is contacted with an atmosphere containing about 50 to 10,000 ppm by volume of said fluorine interhalogen compound.

4. A method as claimed in claim 3 in which the atmosphere contains about 100 to about 1000 ppm by volume of said fluorine interhalogen compound.

5. A method as claimed in claim 1 in which the atmosphere additionally comprises an inert gas.

6. A method as claimed in claim 5 wherein said inert gas is selected from the group consisting of nitrogen, carbon dioxide and air.

7. A method as claimed in claim 5 in which the inert gas is nitrogen.

8. A method as claimed in claim 1 in which the surface is exposed to a humid gaseous atmosphere immediately prior to or during exposure of the surface to the fluorine interhalogen compound.

9. A method as claimed in claim 7 in which the humid gaseous atmosphere has a relative humidity above about 65% at about ambient room temperature.

10. A method as claimed in claim 1 in which the surface is contacted with the gaseous chlorine trifluoride for at least about 15 minutes to about 4 hours.

11. A method as claimed in claim 7 in which the humid gaseous atmosphere has a relative humidity of about 65% to about 95% and wherein the surface is exposed to said humid gaseous atmosphere for at least about 15 minutes immediately before exposure to the said fluorine interhalogen compound.

12. A method as claimed in claim 2 in which said fluorine interhalogen compound is chlorine trifluoride.

13. A method as claimed in claim 1 in which said chlorofluoride is chlorine pentafluoride. fluorine interhalogen compound is chlorine pentafluoride.

14. A method as claimed in claim 2 in which said fluorine interhalogen compound is chlorine pentafluoride.

15. A method as claimed in claim 2 in which said fluorine interhalogen compound is iodine heptafluoride.

16. A method as claimed in claim 2 in which said fluorine interhalogen compound is bromine trifluoride.

17. A method as claimed in claim 2 in which said fluorine interhalogen compound is bromine pentafluoride.

18. A method for sterilizing the surface of an article contaminated with bacterial spores comprising the steps of exposing said surface, to an effective amount of at least one gaseous chlorofluoride for 2 time period sufficient to kill said spores.

19. A method as claimed in claim 19 in which said chlorofluoride is gaseous chlorine trifluoride.

20. A method as claimed in claim 19 in which the surface is contacted with an atmosphere containing about 50 to about 10,000 ppm by volume of gaseous chlorine trifluoride.

21. A method as claimed in claim 20 in which the atmosphere contains about 100 to 1000 ppm by volume gaseous chlorine trifluoride.

22. A method as claimed in claim 20 in which the atmosphere additionally comprises an inert gas selected from the group consisting of nitrogen, carbon dioxide and air.

23. A method as claimed in claim 22 in which the inert gas is nitrogen.

24. A method as claimed in claim 19 in which the surface is exposed to a humid gaseous atmosphere immediately prior to or during exposure of the surface to the gaseous chlorine trifluoride.

25. A method as claimed in claim 24 in which the humid gaseous atmosphere has a relative humidity above about 65% at about ambient room temperature.

26. A method as claimed in claim 19 in which the surface is contacted with the gaseous chlorine trifluoride for at least about 15 minutes to about 4 hours.

27. A method as claimed in claim 24 in which the humid gaseous atmosphere has a relative humidity of about 65% to about 95% and wherein the surface is exposed to said humid gaseous atmosphere for at least about 15 minutes immediately before exposure to the gaseous chlorine trichloride.

28. A method as claimed in claim 18 in which said chlorofluoride is chlorine pentafluoride.

29. A method as claimed in claim 28 in which the effective amount of chlorine pentafluoride is about 50 to 10,000 ppm by volume.

30. A method as claimed in claim 29 in which the effective amount of chlorine pentafluoride is about 100 to 1000 ppm by volume.

31. A method as claimed in claim 18 in which the gaseous chlorofluoride is a mixture of chlorine trifluoride and chlorine pentafluoride.

32. A method for sterilizing the surface of an article contaminated with bacterial spores comprising the steps of exposing the surface to a humid gaseous atmosphere having a relative humidity of at least about 65% for at least 15 minutes, and immediately exposing said surface to an effective amount of gaseous chlorine trifluoride for a time period of at least about 15 minutes to kill the spores.

33. A method for sterilizing the surface of an article contaminated with bacterial spores comprising the steps of exposing the surface to a humid gaseous atmosphere having a relative humidity of at least about 65% for at least 15 minutes, and immediately exposing said surface to an effective amount of gaseous chlorine pentafluoride for a time period of at least about 15 minutes to kill the spores.

* * * * *